United States Patent [19]

Oyama et al.

[11] 4,284,721

[45] Aug. 18, 1981

[54] METHOD FOR MANUFACTURING DIPEPTIDES

[75] Inventors: Kiyotaka Oyama, Shin-nanyo; Shigeaki Nishimura, Kudamatsu; Yuji Nonaka, Shin-nanyo; Tsutomu Hashimoto; Keiichi Kihara, both of Tokuyama, all of Japan

[73] Assignees: Sagami Chemical Research Center; Ajinomoto Co., Inc., both of Tokyo; Toyo Soda Mfg. Co., Ltd., Yamaguchi, all of Japan

[21] Appl. No.: 136,347

[22] Filed: Apr. 1, 1980

[30] Foreign Application Priority Data

Apr. 3, 1979 [JP] Japan .................................. 54-40170

[51] Int. Cl.$^3$ ..................... C12P 21/02; C07C 103/52
[52] U.S. Cl. ................................. 435/70; 260/112.5 R
[58] Field of Search ..................... 260/112.5 R; 435/70

[56] References Cited

U.S. PATENT DOCUMENTS

| | | | |
|---|---|---|---|
| 3,972,773 | 8/1976 | Isowa et al. | 435/70 |
| 4,119,493 | 10/1978 | Isowa et al. | 435/70 |

FOREIGN PATENT DOCUMENTS 2801238  8/1978  Fed. Rep. of Germany ............. 435/70

OTHER PUBLICATIONS

A. M. Kibanov et al., Biotechnology and Bioengineering, 19, 1351–1361 (1977).
R. Okachi et al., Kagaku to Seibutsu 16 (8) 536–546 (1978).

*Primary Examiner*—Delbert R. Phillips
*Attorney, Agent, or Firm*—Armstrong, Nikaido, Marmelstein & Kubovcik

[57] ABSTRACT

An improvement in a method for manufacturing dipeptides from an N-substituted aspartic acid and a phenylalanine lower alkyl ester. The two starting materials are allowed to react with each other in the presence of an immobilized metallo-proteinase in an organic solvent immiscible with water. The enzyme can be recovered for reuse thereof. The loss of materials due to the hydrolysis of the phenylalanine lower alkyl ester is reduced, so that use of the phenylalanine lower alkyl ester in a nearly stoichiometric quantity suffices for the reaction to ensure an improved yield and reduction in cost of industrial production.

10 Claims, No Drawings

METHOD FOR MANUFACTURING DIPEPTIDES

BACKGROUND OF THE INVENTION

1. Field of the Invention

This invention relates to a method for manufacturing dipeptides and more particularly to a method in which an N-substituted aspartic acid and a lower alkyl ester of phenylalanine are subjected to reaction carried out in an organic solvent using an immobilized enzyme to produce a dipeptide.

2. Description of the Prior Art

Enzymes are proteinous compounds which function to catalyze vital reactions to an extremely great degree. Generally, however, the enzymes are not only expensive but also unstable and thus have been utilized in a very narrowly limited range of reactions for industrial purposes. In view of the excellent catalytic function of the enzymes, researches for their industrial applications have recently been actively conducted. As a result of such researches, it has become possible to improve the enzyme stability by immobilizing them. Further, their repeated use and continuous processes for the reaction also have become possible to permit their utilization for industrial purposes. However, in an organic solvent, the activity of the enzymes are very low. Besides, they easily become denatured and deactivated in the organic solvent. Hence, the use of the enzymes have been restricted to an aqueous medium. Thus there has been great restriction also in that respect.

In relation to an enzymatic reaction in an organic solvent, it is known to obtain acetyl-L-tryptophan ethyl ester from acetyl-L-tryptophan and ethyl alcohol.

Further, it has long been known that a proteolytic enzyme serves to catalyze a peptide linkage forming reaction in an aqueous medium. However, there has been no report on such a reaction in an organic solvent. Meanwhile the present inventors have previously proposed a method in which an N-substituted monoaminodicarboxylic acid is reacted with an aminocarboxylic acid ester in an aqueous solvent in the presence of a proteolytic enzyme; then the thus resulting dipeptide ester and the aminocarboxylic acid ester are allowed to form an addition compound; and the addition compound is separated. This method is disclosed in Japanese unexamined patent application publication No. 92729/1978.

The present inventors conducted further studies for such reactions and discovered that a peptide linakge forming reaction could be efficiently carried out by allowing an N-substituted aspartic acid and a phenylalanine lower alkyl ester to react in an organic solvent immiscible with water in the presence of an immobilized metallo-proteinase containing water. The present invention is derived from this discovery.

SUMMARY OF THE INVENTION

It is an object of this invention to provide a method for manufacturing a dipeptide in which an N-substituted aspartic acid and a phenylalanine lower alkyl ester are allowed to react with each other in an organic solvent immiscible with water in the presence of a water-containing immobilized metallo-proteinase to produce the dipeptide ester.

It is another object of this invention to provide a method for manufacturing a dipeptide in which an N-substituted aspartic acid and a phenylalanine lower alkyl ester are contacted with a water-containing immobilized metallo-proteinase in an organic solvent immiscible with water to couple both components to produce the dipeptide.

In the invented method, the N-substituent group of the N-substituted aspartic acid is a protective group for amino groups which is ordinarily used in a peptide synthesis. Examples of preferable protective groups are urethane type protective groups such as benzyloxycarbonyl group, p-methoxybenzyloxycarbonyl group, t-butoxycarbonyl group, etc. The lower alkyl group of the phenylalanine lower alkyl ester which is employed as the other starting material is an alkyl group of $C_1$–$C_4$ and especially, it is exemplified by a methyl group and an ethyl group as preferable ones. Further, both of the materials may be in an L or DL configuration. Where DL isomers are employed, it is only the L isomer that participates in the reaction while the D isomer remains unreacted in the solution.

The enzyme used in accordance with the method of this invention in the form of immobilized enzyme is a proteolytic enzyme having a metal ion at the active center thereof or, in other words, a metallo-proteinase. Examples of the enzymes are those originating from microorganisms such as a neutral protease, originating from actinomycetes, prolysine, thermolysin, collagenase, crotulus atrox protease, etc. A crude enzyme such as thermoase is also usable. In using such a crude enzyme, a potato-inhibitor or a like inhibitor may be used to inhibit the action of contaminating esterase or the like. In accordance with the present invention, however, it is most preferable to use thermolysin or thermoase.

In the invented method, these enzymes are used in an immobilized form, where those obtained through an ordinary immobilizing method are usable. Such immobilizing methods include a physical adsorption method, an ionic bonding method, a covalent boding method, an inclusion method, and a cross linking method. However, the immobilizing method is not limited to these methods but the enzymes which are merely carried on a porous carrier that has a very weak interaction with the enzymes may be employed.

The term "immobilized enzyme", hereinafter referred to, means a complex comprising the enzyme and a carrier.

The quantity of the enzyme to be carried on a carrier cannot necessarily be determined on a simple basis because the enzyme-carrying ability of the carrier depends on the intensity of interaction between the carrier and the enzyme. However, the quantity may be about 1 about 2,000 mg and usually about 50 to about 1,000 mg per g quantity of the carrier on a dry basis. However, the above mentioned quantities are not limitative and especially as to the upper values, a carrier which is capable of carrying the enzyme in a quantity more than the above values is rather preferable if it is available, because it is possible to reduce the carrier consumption. Since the enzyme of the immobilized enzyme to be used in accordance with the present invention exert very low activity in a dry organic solvent and is unstable, it is necessary to have the insides of the pores of the immobilized enzyme filled with water when used in the organic solvent. The water contained in the pores should have a pH value that allows the metallo-proteinase to exert its activity. Since the optimum pH value of the metallo-proteinase is in a neutral region, the water may contain a buffer agent capable of keeping the desired pH value (pH about 5–about 9).

Although there is no particular restriction on the water content of the immobilized enzyme, the water content is usually within a range from about 1 to about 500% by weight and preferably from about 10 to about 200% by weight based on the carrier on a dry basis. Further, for this purpose, it is also possible to utilize water which is naturally captured into the carrier when the enzyme is carried on the carrier in an aqueous solution for the immobilized enzyme preparation.

The solvent used in the invented method is an organic solvent that is immiscible with water. The use of an organic solvent miscible with water is not desirable except for the use as an additive to the organic solvent immiscible with water as mentioned hereinbelow, because if it is employed, the water held in the pores of the immobilized enzyme comes to dissolve into the organic solvent and thus would be replaced to hinder the reaction. Even in using the organic solvent immiscible with water, it is still preferable to be saturated with water to ensure that it does not dissolve to deprive of the water from the pores. In this sense, the organic solvent immiscible with water as used in the present invention means in another term an organic solvent or a homogenous mixture of the organic solvent and water that dissolves very little water when it is brought into contact with a small amount of water. Therefore, so long as such a condition is not disturbed, it is possible to add an organic solvent miscible with water to the organic solvent immiscible with water. Further, in accordance with the invention, it is necessary that the organic solvent immiscible with water has an ability to dissolve both of the starting materials and the reaction product. Examples of preferable organic solvents are a lower alkyl halide such as chloroform, ethylenedichloride; an ester of carboxylic acid, such as ethyl acetate, isopropyl acetate; a ketone such as methylisobutyl ketone; an aromatic hydrocarbon such as benzene, toluene; and a mixture of them. As mentioned in the foregoing, so long as the condition that the solvent be immiscible with water is preserved, a solvent such as ethanol that is miscible with water may be added to those solvents.

It is preferable to have a high concentration of each one of the starting materials to be used in accordance with the invented method, because the higher the concentration the faster the reaction rate will be. Each starting material is usually used in a concentration within the solubility thereof in the solvent. However, since the materials are consumed as the reaction proceeds, it is possible to have a portion of them in a suspended state in the solvent. It is convenient to use each material in a concentration ranging from about 0.001 M to about 2 M in general and preferably between about 0.01 M and about 0.5 M.

The quantity of the N-substituted aspartic acid and that of the phenylalanine lower alkyl ester to be used in accordance with the invented method can be usually in a stoichiometric ratio of 1:1 in mol ratio when both substrates are in L configuration. Practically, they may be used in a ratio ranging between 10:1 and 1:10 and preferably between 3:1 and 1:5. In cases where the materials are in a DL configuration, they may be used in quantities which result in the ratio of the L-isomers ranging in the above stated ratios.

There is no particular restriction on the quantity of the water-containing immobilized enzyme to be used in accordance with the invented method. A higher concentration of it permits the reaction to be completed in a shorter period of time while a lower concentration of it makes the reaction time longer. The quantity of it to be used also depends on the quantity of the enzyme carried on the carrier and its activity. For example, comparing a case where the immobilized enzyme prepared from the enzyme and a carrier which exerts no particular interaction with the enzyme is used with another case where the immobilized enzyme prepared from the enzyme and a carrier strongly adsorbing the enzyme, such as a matrix of acrylic ester is used, the latter has a greater quantity of the enzyme than the former. Therefore, the latter can give a comparable effect with the use of a less quantity than in the former case. Generally, however, for 1 millimol of each starting material, the use of about 0.01 g to about 20 g and preferably about 0.1 g to about 5 g of the water-containing immobilized enzyme suffices.

The invented method can be carried out, for example, by allowing the water-containing immobilized enzyme to suspend in the organic solvent immiscible with water which contains both of the starting materials therein and then by allowing the reaction to proceed with stirring. Upon completion of the reaction, the immobilized enzyme and a reaction mixture solution containing a reaction product can be separated from each other by subjecting the reacted mixture suspension to a filtration process, etc.

The invented method can also be carried out in a column filled with the water-containing immobilized enzyme, by allowing the organic solvent immiscible with water which contains the two starting materials therein to flow through the filling layer of the column. This process permits the reaction to be continuously carried out and is advantageous for an industrial application of the invented method.

The reaction temperature is usually in the range between about 10 and about 80° C. and preferably between about 20 and about 50° C.

The reaction time depends on the concentrations of the two substrates, the quantity of the immobilized enzyme, the carried enzyme quantity and a predetermined converting rate, etc. However, usually the reaction time of about 0.5 to about 200 hours and preferably about 2 to about 100 hours suffices.

The reaction product, the N-substituted-L-aspartyl-L-phenylalanine lower alkyl ester can be isolated by a conventional means such as concentrating to crystallization, extraction or the like, from the reaction mixture separated from the immobilized enzyme by a suitable process after the reaction according to the method of this invention. Further, since the immobilized enzyme which has been separated from the reaction mixture suspension still has a sufficient activity, it can be used again.

The dipeptides obtained in the method of this invention are useful materials as seen from the case, for example, of the dipeptide having a methyl group as the lower alkyl group, from which dipeptide a sweetening agent, L-aspartyl-L-phenylalanine methyl ester, having a 200 times sweetness as compared with sucrose can be derived by removing the N-substituent by a suitable process.

As apparent from the foregoing, a peptide linkage forming reaction process can be allowed to take place in an organic solvent in accordance with the method of the present invention to permit recovery and reuse of the enzyme without difficulty. Further, since the hydrolysis of the phenylalanine lower alkyl ester is suppressed in the reaction carried out in the organic solvent, there is a less degree of loss of the starting materials as compared with the method of carrying out the reaction in an aqueous medium. Besides, where both of the starting mterials are in L configurations, the stoichiometric ratio of the N-substituted aspartic acid to the phenylalanine lower alkyl ester is 1:2 in mol ratio in the case of the reaction in the aqueous medium as disclosed in the Japanese unexamined patent application publication No. 92729/1978, while the ratio is 1:1 in mol ratio in accordance with the method of the present invention. Accordingly, with the invented method, the phenylalanine lower alkyl ester can be used in lesser quantity. This is a great advantage for an industrial application.

Further, in accordance with the invented method, when the starting materials in DL configurations are used, an enrichment of a D-isomer or D-isomers can be attained as to either one of both starting materials or both of the two starting materials with the simultaneous manufacture of the dipeptide.

The above and further objects, features and advantages of the invention will become apparent from the following detailed description of embodiment examples thereof, which are included merely to aid in the understanding of the invention and variations may be made without departing from the spirit and scope of the invention.

DETAILED DESCRIPTION OF PREFERRED EMBODIMENTS

EXAMPLE 1

First, 3.0 g of Thermoase (titer: 1.6 million PU/g) and 0.15 g of calcium acetate monohydrate were added to 25 ml of a 0.05 M sodium acetate buffer solution of pH 7.5 and were mixed together. A centrifugal sedimentation process was carried out to separate a supernatant liquid and an insoluble matter from each other. To the supernatant liquid thus obtained was added 30 ml (20 g) of a wet acrylic ester matrix carrier ("Amberlite XAD-7," Trademark having about 230% by weight of water content on a dry basis) and the resulting mixture was stirred overnight to obtain an aqueous suspension solution of an immobilized enzyme. The immobilized enzyme which contained water was separated through filtration by suction using a glass filter. The carried quantity of the enzyme in the immobilized enzyme was estimated to be 3 g from the initial quantity of the enzyme and the enzymatic activity of the filtrate measured by a case in digestion method. The water content in the immobilized enzyme thus obtained was almost the same as the initial water content of the carrier. The same method for determining the carried quantity of enzyme was adopted in other Examples hereinbelow given.

The immobilized enzyme thus obtained was added to 37 ml of an ethyl acetate solution saturated with water in advance which contained 3.21 g (12 m mol) of N-benzyloxycarbonyl-L-aspartic acid and 4.14 g (23 m mol of L-phenylalanine methyl ester. Then, a reaction was carried out with gentle stirring for 23 hours at 40° C. After completion of the reaction, the immobilized enzyme was separated by a suction filtration using a glass filter and was washed with 50 ml of ethyl acetate.

The filtrate and the washing were mixed together and washed with 1 N hydrochloric acid (20 ml, twice) and with water (20 ml, once). The ethyl acetate layer thus obtained was dried with sodium sulfate anhydride and condensed. To this was added n-hexane until the liquid showed a white turbid state. Then, the ethyl acetate layer was left standing overnight at room temperature. Resulting crystals of N-benzyloxycarbonyl-L-aspartyl-L-phenylalanine methyl ester were isolated by filtration and then allowed to recrystallize in an ethyl acetate-n-hexane mixture solvent. The yield was 3.71 g (72.3%). Characteristics of the N-benzyloxycarbonyl-L-aspartyl-L-phenylalaninemethyl ester thus obtained were as shown below:

Melting point: 118°–124° C.
$[\alpha]_D^{25}$: $-14.6$ (C=1, methanol)
Elementary analysis
Calculated values (%): C 61.67; H: 5.65; N: 6.54 ($C_{22}H_{24}N_2O_7$); Found values (%): C, 61.53; H: 5.72; N: 6.48.

A part of the ethyl acetate layer was aliquoted beforehand and, after evaporation to dryness, was dissolved in an aqueous solution of sodium acetate (0.8 wt.%). The solution thus obtained was subjected to a high speed liquid chromatography analysis to find that the yield of the N-benzyloxycarbonyl L-aspartyl-L-phenylalanine methyl ester was 84.7% in the reaction.

The measuring apparatus and conditions used for the high speed liquid chromatography analysis were as shown below:

Apparatus: A high speed liquid chromatograph, manufactured by Toyo Soda Manufacturing Co., Ltd. (TSK HLC 802, Trademark)
Column: 7.5 mm in inner dia. and 300 mm in length
Filler: Starch gel of particle size 5μ, manufactured by Toyo Soda Manufacturing Co., Ltd. (TSK GEL, LS-170, P5, Trademark)
Eluent: An aqueous solution of sodium acetate (0.8 wt.%)
Rate of flow: 0.8 ml/min
Pressure loss: 20 kg/cm
Detector: UV 254 nm Unless otherwise stated, the apparatus and conditions mentioned above were also employed in the following Examples for the confirmation of the reaction products and the measurement of yields thereof.

EXAMPLE 2

The preparation of the immobilized enzyme and the reaction were conducted in the same manner as in Example 1 with the exception that: The quantity of Thermoase and that of the calcium acetate monohydrate were 9.0 g and 0.45 g respectively, the quantity of the 0.05 M sodium acetate buffer solution of pH 7.5 was 90 ml; the acrylic ester matrix carrier (Amberlite XAD-7, Trademark) was replaced with 16.6 g of another carrier of the similar class (Amberlite XAD-8, Trademark, containing about 150 wt.% of water on a dry basis; the quantity of N-benzyloxycarbonyl-L-aspartic acid was 2.14 g (8 m mol): L-phenylalanine methyl ester was replaced with 2.87 g (16 m mol) of DL-phenylalanine methyl ester; the quantity of the water saturated ethyl acetate solution was changed to 26 ml; and the reaction time was five fours. N-Benzyloxycarbonyl-L-aspartyl-L-phenylalanine methyl ester was obtained in the yield of 79.8%.

The enzyme quantity carried on the immobilized enzyme prepared and used in this Example was about 6 g. The water content thereof was almost the same as the initial water content of the carrier.

EXAMPLE 3

The preparation of the immobilized enzyme and the reaction were carried out in the same manner as in Example 2 with the exception that: In place of the ethyl acetate solution employed in Example 2, 50 ml of water saturated methyl-isobutyl ketone was used; the reaction time was 3 hours; and the washing of the immobilized enzyme after completion of the reaction was carried out with methyl-isobutyl ketone. N-Benzyloxycarbonyl-L-aspartyl-L-phenylalaninemethyl ester was obtained in the yield of 41.0%.

The quantity of the enzyme carried on the immobilized enzyme which was prepared and used in this Example and the water content of the immobilized enzyme were about the same as in Example 2.

EXAMPLE 4

The preparation of the immobilized enzyme and the reaction were carried out in the same manner as in Example 2 with the exception that: The quantity of Thermoase and that of the calcium acetate monohydrate were 7.0 g and 0.35 g, respectively; in place of the N-benzyloxycarbonyl-L-aspartic acid, 3.56 g (12 m mol) of N-p-methoxybenzyloxycarbonyl-L-aspartic acid was used while the DL-phenylalaninemethyl ester was replaced with 4.30 g (24 m mol) of L-phenylalanine methyl ester; the quantity of the water saturated ethyl acetate solution was 39 ml; and the reaction temperature was 25° C. Upon completion of the reaction, the immobilized enzyme was separated by suction filtration using a glass filter and then the immobilized enzyme was washed with 50 ml of ethyl acetate. The filtrate and the washing liquid were treated in the same manner as in Example 1 and N-p-methoxybenzyloxycarbonyl-L-aspartyl-L-phenylalaninemethyl ester was isolated to obtain 3.93 g of crystals (yield: 71.5%). The quantity of enzyme carried on the immobilized enzyme prepared and used in this Example and the water content thereof were about the same as in Example 2. Characteristics of the N-p-methoxybenzyloxycarbonyl-L-aspartyl-L-phenylalanine methyl ester thus obtained were as shown below:

Melting point: 125°–129° C.
$[\alpha]_D^{25}$: −11.5 (C=1, methanol)
Elementary analysis
Calculated values (%): C 60.25; H; 5.72; N: 6.11 ($C_{23}H_{26}N_2O_8$); Found values (%): C: 60.43; H; 5.80; N: 5.90.

Further, the yield of the formation of N-p-methoxybenzyloxycarbonyl-L-aspartyl-L-phenylalaninemethyl ester was measured by the high speed liquid chromatography in the same manner as in Example 1. The measurement gave the yield of 81.3%.

EXAMPLE 5

The preparation of the immobilized enzyme and the reaction were carried out in the same manner as in Example 4 with the exception that: The sodium acetate buffer solution used in Example 4 was replaced with 70 ml of distilled water; N-p-methoxybenzyloxycarbonyl-L-aspartic acid was replaced with 3.21 g (12 m mol) of N-benzyloxycarbonyl-L-aspartic acid; and the quantity of the L-phenylalaninemethyl ester was changed to 2.15 g (12 m mol) and the reaction time at 24 hours. N-Benzyloxycarbonyl-L-aspartyl-L-phenylalaninemethyl ester was obtained in the yield of 74.8%.

The quantity of enzyme carried on the immobilized enzyme prepared and used in this Example and the water content thereof were about the same as in Example 2.

EXAMPLE 6

The preparation of the immobilized enzyme and the reaction were carried out in the same manner as in Example 1 with the exception that: The ethyl acetate was replaced with a water-saturated isopropyl acetate solution; the reaction time was changed to 21.5 hours; and the washing liquid used for washing the immobilized enzyme after completion of the reaction was changed to isopropyl acetate. N-Benzyloxycarbonyl-L-aspartyl-L-phenylalaninemethyl ester was obtained in the yield of 82.0%.

The quantity of enzyme carried on the immobilized enzyme prepared and used in this Example and the water content thereof were about the same as in Example 1.

EXAMPLE 7

The immobilized enzyme was prepared and the reaction was carried out in the same manner as in Example 1 with the exception that: The quantity of Thermoase and that of the calcium acetate monohydrate were changed to 2 g and 0.1 g, respectively; the sodium acetate buffer solution was replaced with 20 ml of a 0.05 M Tris-hydrocyloric acid buffer solution of pH 8.0. The acrylic ester matrix carrier was replaced with 3 g of dry porous glass beads measuring 500 A in pore diameter, manufactured by Electro-Nucleonix Company, "CPG-10"); the length of time used for preparation of the immobilized enzyme was changed to one hour. The quantities of N-benzyloxycarbonyl-L-aspartic acid and L-phenylalaninemethyl ester were changed to 0.08 g (0.3 m mol) and 0.109 g (0.61 m mol) respectively; the ethyl acetate was replaced with 30 ml of water saturated chloroform; the reaction time was changed to 21 hours; and the washing liquid used for washing the immobilized enzyme after completion of the reaction was changed to chloroform. N-Benzyloxycarbonyl-L-aspartyl-L-phenylalaninemethyl ester was obtained in the yield of 20.1%.

The quantity of enzyme carried on the immobilized enzyme was about 0.7 g and the water content thereof was about 150 wt.% on a dry basis.

EXAMPLE 8

The immobilized enzyme was prepared and the reaction was carried out in the same manner as in Example 1 with the exception that: The quantities of Thermoase and the calcium acetate monohydrate were 1.0 g and 0.05 g respectively; the sodium acetate buffer solution was replaced with 10 ml of a buffer solution of 0.05 M Tris-hydrochloric acid of pH 8.0; the acrylic ester matrix carrier was replaced with 3 g of dry porous glass beads 500 A in pore diameter, manufactured by Electro-Nucleonix Co., "CPG-10"); the length of time used for the preparation of the immobilized enzyme was changed to one hour; the quantity of L-phenylalaninemethyl ester was 3.94 g (22 m mol) and that of the water saturated ethyl acetate solution) was 43 ml; and the reaction time was 65 hours. N-Benzyloxycarbonyl-L-aspartyl-L-phenylalaninemethyl ester was obtained in the yield of 74.2%.

The enzyme quantity carried on the immobilized enzyme prepared and used in this Example and the water content thereof were about the same as in Example 7.

EXAMPLE 9

The reaction was carried out in the same manner as in Example 8 with the exception that: The immobilized enzyme which was separated and recovered after completion of the reaction carried out in Example 8 was employed for the reaction; and the reaction was allowed to proceed for 93 hours. The yield of N-benzyloxycarbonyl-L-asparty-L-phenylalaninemethyl ester thus obtained was 88.0%.

EXAMPLE 10

The immobilized enzyme was prepared and the reaction was carried out in the same manner as in Example 1 with the exception that: The quantities of Thermoase and the calcium acetate monohydrate were 4 g and 0.2 g respectively; the quantity of the buffer solution of 0.05 M sodium acetate of pH 7.5 was 40 ml; the acrylic ester matrix carrier was replaced with 15 ml (11.7 g) of a wet hydrophilic gel (TOYOPEARL 5, trademark manufactured by Toyo Soda Manufacturing Co., Ltd., containing about 230 wt.% of water on a dry basis) having a carboxymethyl group; the length of time used for the preparation of the immobilized enzyme was one hour; the L-isomer of N-benzyloxycarbonylaspartic acid was replaced with DL-isomers thereof; and the reaction time was 22 hrs. N-Benzyloxycarbonyl-L-aspartyl-L-phenylalaninemethyl ester was obtained in the yield of 41.0%.

The enzyme quantity carried on the immobilized enzyme prepared and used in this Example was about 0.9 g and the water content thereof was almost the same as the initial water content of the carrier.

EXAMPLE 11

The immobilized enzyme was prepared and the reaction was carried out in the same manner as in Example 1 with the exception that: In place of the acrylic ester matrix carrier employed in Example 1, 15 ml (11.7 g) of a wet hydrophilic gel (TOYOPEARL 5, Trademark), manufactured by Toyo Soda Manufacturing Co., Ltd., containing about 230 wt.% of water on a dry basis) having a diethylaminoethyl group was used. The immobilized enzyme preparation time was 5 hours. The L-isomers of N-benzyloxycarbonylaspartic acid and phenylalaninemethyl ester, both employed in Example 1 were replaced with DL-isomers thereof. The reaction time was 22.5 hours. N-Benzyloxycarbonyl-L-aspartyl-L-phenylalaninemethyl ester was obtained in the yield of 25.5%.

The enzyme quantity carried on the immobilized enzyme prepared and used in this example was about 1.0 g while the water content thereof was almost the same as that of the carrier in the initial stage.

EXAMPLE 12

The immobilized enzyme was prepared and the reaction was carried out in the same manner as in Example 1 with the exception that: In place of the buffer solution of 0.05 M sodium acetate of pH 7.5 employed in Example 1, 25 ml of a buffer solution of 0.1 M sodium acetate of pH 6.0 was used; the acrylic ester matrix carrier employed in Example 1 was replaced with 15 ml (11.7 g) of a wet hydrophilic carrier which showed a very weak interaction with the enzyme (TOYOPEARL-5, trademark, manufactured by Toyo Soda Manufacturing Co., Ltd., containing about 230 wt.% of water on a dry basis); and in the preparation of the immobilized enzyme, 0.6 g of a potato-inhibitor was added. N-Benzyloxycarbonyl-L-aspartyl-L-phenylalaninemethyl ester was obtained in the yield of 55.5%.

The enzyme quantity carried on the immobilized enzyme prepared and used in this Example was about 0.8 g while the water content thereof was almost the same as the water content in the carrier in the initial stage thereof.

EXAMPLE 13

The immobilized enzyme was prepared in the same manner as in Example 1 with the exception that: The quantities of the Thermoase and the calcium acetate monohydrate were 2.0 g and 0.1 g respectively; the sodium acetate buffer solution was replaced with 20 ml of distilled water; the carrier which was an acrylic ester matrix was replaced with 11.7 g of a wet hydrophilic gel (TOYOPEARL-5, trademark manufactured by Toyo Soda Manufacturing Co., Ltd., containing about 230 wt.% of water on a dry basis) having an epoxide group; and an aqueous solution of sodium hydroxide was added to the suspension to adjust it to be of pH 8.0. The quantity and the water content of the immobilized enzyme were the same as in Example 12.

Further, the reaction was carried out in the same manner as in Example 1 with the exception that: The quantities of N-benzloxycarbonyl-L-aspartic acid and L-phenylalaninemethyl ester were 2.14 g (8 m mol) and 2.87 g (16 m mol), respectively; the quantity of the water-saturated ethyl acetate was 26 ml; and the reaction time was 28.5 hours. Through this reaction, N-benzyloxycarbonyl-L-aspartyl-L-phenylalaninemethyl ester was obtained in the yield of 82.9%.

EXAMPLE 14

The immobilized enzyme was prepared and the reaction was carried out in the same manner as in Example 1 with the exception that: Thermoase was replaced with 0.45 g of thermolysin (having titer of 8.080 PU/mg, a product of Daiwa Kasei K.K.); in place of the carrier which was an acrylic ester matrix carrier, 15.6 g of a wet hydrophilic gel (TOYOPEARL-7 (trademark) manufactured by Toyo Soda Manufacturing Co., Ltd., about 230 wt.% of water content on a dry basis.) was used. N-Benzyloxycarbonyl-L-aspartyl-L-phenylalaninemethyl ester was obtained in the yield of 59.8%.

The quantity of enzyme carried on the immobilized enzyme prepared and used in this Example was about 0.15 g while the water content thereof was almost the same as that in the initial stage thereof.

EXAMPLE 15

The immobilized enzyme was prepared and the reaction was carried out in the same manner as in Example 4 with the exception that: The sodium acetate buffer solution employed in Example 4 was replaced with 70 ml of distilled water; N-p-methoxybenzyloxycarbonyl-L-aspartic acid was replaced with 2.80 g (12 m mol) of N-t-butoxycarbonyl-L-aspartic acid; the reaction temperature was 40° C.; and the reaction time at 23 hours. The immobilized enzyme thus prepared and used in this Example had the same enzyme quantity and water content as in Example 4.

The filtrate form which the immobilized enzyme was removed and the washing liquid used were mixed together. Then, from the mixture liquid, N-t-butoxycarbonyl-L-aspartyl-L-phenylalaninemethyl ester was isolated in the same manner as in Example 1. The yield was 1.4 g (29.6%). Characteristics of the N-t-butoxycarbonyl-L-aspartyl-L-phenylalaninemethyl ester were as shown below:

Melting point: 149°–150° C.
$[\alpha]_D^{25}$: −15.3(C=1, methanol)
Elementary analysis
Calculated values: C: 57.85; H: 6.65; N: 7.10 ($C_{19}H_{26}N_2O_7$); Found values: C: 58.03; H: 6.56; N: 7.05.

Further, a part of the ethyl acetate layer was aliquoted and, after dryed and dissolved in a sodium acetate solution (0.8 wt.%), was subjected to the analysis in the same manner as in Example 1. N-t-Butoxycarbonyl-L-aspartyl-L-phenylalaninemethyl ester was obtained in the yield of 52.6%.

EXAMPLE 16

The immobilized enzyme was prepared and the reaction was carried out in the same manner as in Example 7 with the exception that chloroform, the solvent used for the peptide linkage formation reaction was changed to toluene. In this Example, N-benzyloxycarbonyl-L-aspartyl-L-phenylalaninemethyl ester was obtained in this yield of 10.5%.

EXAMPLE 17

The immobilized enzyme was prepared in the same manner as in Example 1 with the exception that: The quantities of Thermoase and the calcium acetate monohydrate were 21.0 g and 1.05 g, respectively; the buffer solution of sodium acetate was replaced with 210 ml of distilled water; the quantity of the acrylic ester matrix carrier (Amberlite XAD-7, trademark, containing 230% of water on a dry basis) was 100 g; and a length of time for stirring the enzyme solution containing the carrier was four hours. The enzyme quantity carried on the immobilized enzyme thus obtained was about 20 g. The water content thereof was almost the same as the initial water content of the carrier.

A flowing type glass column which measured 24 mm in inner dia. and 300 mm in height and which was provided with a jacket disposed on the outside thereof for thermal insulation was filled with thus obtained immobilized enzyme. Then, 700 g of an ethyl acetate solution saturated with water and kept at 35° C. which contained 74 g of L-phenylalaninemethyl ester and 55 g of N-benzyloxycarbonyl-L-aspartic acid was passed through this column at a flaw rate of about 0.3 ml per min while the jacket was kept at 40° C. for the reaction. Then, after 17 hours from the commencement of the reaction, the effluent from the column contained N-benzyloxycarbonyl-L-aspartyl-L-phenylalaninemethyl ester with the yield of 54.3%.

What is claimed is:

1. A method for manufacturing a dipeptide from an N-substituted aspartic acid and a phenylalanine lower alkyl ester, said method comprising subjecting said N-substituted aspartic acid and said phenylalanine lower alkyl ester to a reaction in an organic solvent immiscible with water in the presence of a water-containing immobilized metallo-proteinase.

2. A method for manufacturing a dipeptide according to claim 1, wherein the N-substituted aspartic acid and the phenylalanine lower alkyl ester are contacted with the water-containing immobilized metallo-proteinase in the organic solvent immiscible with water, thereby coupling both components.

3. A method for manufacturing a dipeptide according to claim 1 or 2, wherein the substituent of said N-substituted aspartic acid is an urethane type substituent.

4. A method for manufacturing a dipeptide according to claim 2 wherein the substituent in said N-substituted aspartic acid is a benzyloxycarbonyl group, a p-methoxybenzyloxycarbonyl group or a t-butoxycarbonyl group.

5. A method for manufacturing a dipeptide according to claim 1 wherein said N-substituted aspartic acid is in an L-configuration and/or a DL-configuration.

6. A method for manufacturing a dipeptide according to claim 1 wherein said phenylalanine lower alkyl ester is in an L-configuration and/or a DL-configuration.

7. A method for manufacturing a dipeptide according to claim 1 wherein the lower alkyl group of said phenylalanine lower alkyl ester is a methyl group.

8. A method for manufacturing a dipeptide according to claim 1 wherein said metallo-proteinase is thermolysin.

9. A method for manufacturing a dipeptide according to claim 1 wherein said metallo-proteinase is thermoase.

10. A method for manufacturing a dipeptide according to claim 1 wherein said organic solvent immiscible with water is a lower alkyl halide, an ester of carboxylic acid, a ketone, an aromatic hydrocarbon or a mixture thereof.

* * * * *